United States Patent

Watson

[11] Patent Number: 6,145,371
[45] Date of Patent: Nov. 14, 2000

[54] GAS SENSOR

[76] Inventor: Joseph Watson, 22, Valley View Sketty, Swansea, SA2 8BG, United Kingdom

[21] Appl. No.: 09/248,467
[22] Filed: Feb. 11, 1999

[30] Foreign Application Priority Data

Feb. 11, 1998 [GB] United Kingdom ................ 9802940

[51] Int. Cl.⁷ .......................... G01N 27/12; G01N 31/12; G01N 27/00
[52] U.S. Cl. ...................... 73/31.06; 73/23.21; 73/31.05; 422/90
[58] Field of Search ............... 73/31.06, 31.05, 73/335.05, 335.03, 23.31, 23.32, 31.01, 23.21; 422/83, 90, 94

[56] References Cited

U.S. PATENT DOCUMENTS

| 4,600,660 | 7/1986 | Klatt et al. ............................ 428/607 |
| 4,692,385 | 9/1987 | Johnson .................................. 428/469 |
| 5,573,960 | 11/1996 | Izumi et al. ............................. 437/21 |
| 5,591,321 | 1/1997 | Pyke ....................................... 205/787 |
| 5,627,305 | 5/1997 | Yun et al. ............................... 73/23.2 |
| 5,635,628 | 6/1997 | Fleischer et al. ....................... 73/31.06 |
| 5,686,342 | 11/1997 | Lee .......................................... 437/62 |
| 5,734,091 | 3/1998 | Kudo et al. ............................. 73/23.2 |
| 5,767,386 | 6/1998 | Lemire et al. .......................... 73/23.2 |
| 5,821,402 | 10/1998 | Okajima et al. ........................ 73/23.2 |
| 5,824,271 | 10/1998 | Frank et al. ............................ 422/98 |
| 5,866,075 | 2/1999 | Gupta et al. ............................ 422/88 |
| 5,866,800 | 2/1999 | Park et al. .............................. 73/31.06 |

FOREIGN PATENT DOCUMENTS

19652070A1  6/1997  Germany .

Primary Examiner—Hezron Williams
Assistant Examiner—J. David Wiggins
Attorney, Agent, or Firm—David P. Gordon; David S Jacobson; Thomas A Gallagher

[57] ABSTRACT

A gas sensor includes a substrate preferably made of beryllium oxide which is both an electrical insulator and thermal conductor, the substrate having thereon at least one heating element for the substrate, at lease one gas-sensitive active material deposited on the substrate and a set of at least two space electrodes in contact with the active material. The thermal conductivity of the substrate as arranged together with the heating element cooperate and assists to ensure that the substrate achieves a desired thermal gradient while the sensor establishes a near-uniform temperature throughout substantially the entire sensor, thus enabling the operating temperature of the active material to be maintained substantially constant throughout its entire volume.

14 Claims, 3 Drawing Sheets

GAS SENSOR

FIELD OF THE INVENTION

The present invention is concerned with sensors for detecting and monitoring gases, vapors or the like.

STATE OF THE ART

Many solid state gas sensors are known in the art; such sensors are produced by deposition of gas sensitive active materials, electrodes and heat arrays on appropriate substrates. The most common substrate known in the art is aluminum oxide; also known as substrates are silicon, silicon dioxide and silicon nitride.

Such solid-state gas sensors are described in K. Ihokura and J. Watson, "The Stannic Oxide Gas Sensor", (CRC Press, 1994).

Prior art sensors are generally associated with electronic circuits which, via contact electrodes, determine changes in the conductance of resistance of the gas-sensitive active material in the presence of gases or vapors.

However, we have established that the most common substrate, aluminum oxide, has the disadvantage that it is a thermal insulator. The heat conduction within the substrate is poor, which causes temperature gradients within the sensor. This in turn results in the sensitivity and selectivity properties of the active material to be undesirably impaired.

OBJECTS OF THE INVENTION

It is therefore an object of the present invention to provide a sensor for gases, vapors or the like which is sensitive and has good selective properties.

It is further an object of the present invention to provide a sensor for gases, vapors or the like which can be substantially free of undesirable temperature gradients.

SUMMARY OF THE INVENTION

According to the present invention there is provided a gas sensor which includes a substrate which is both an electrical insulator and a thermal conductor, the substrate having thereon:

(i) heating means for the substrate;
(ii) at least one gas-sensitive active material deposited on the substrate; and
(iii) a set of at least two spaced electrodes in contact with said active material.

The thermal conductivity of the substrate can help to ensure that the sensor establishes a near-uniform temperature throughout substantially the entire sensor, thus enabling the operating temperature of the active material to be maintained substantially constant throughout its volume.

Typically, each set of conductors is provided with means for monitoring the electrical conductance between the respective conductor. Such monitoring means typically provide an output such as a warning signal or the like, or an output giving a quantitative indication.

Typically, the substrate is of a refractory or ceramic material, which may be in the form of an oxide. A preferred example of such an oxide is beryllium oxide, an alternative material is aluminum nitride. Such materials are advantageously both thermal conductors and electrical insulators. The substrate is typically in the form of a substantially monolithic body.

The active material is typically deposited on one major surface (only) of the substrate.

The heating means present on the substrate typically includes one or more heating elements, which may be electrical resistance heating elements. Such elements may be made from a metal such as a noble metal (for example, platinum) or from an electrically conductive compound such as ruthenium dioxide.

According to a first embodiment of the present invention the substrate is typically a substantially monolithic body, which is preferably substantially disc or tablet shaped.

According to a second embodiment of the present invention, such a substantially monolithic body may be in the form of an elongate tile. In this embodiment, a heating element is typically arranged towards one end of the tile, with the other end being devoid of heating elements. This enables a desired thermal gradient to be created along the length of the tile.

Advantageously, different active materials can be deposited along the length of such a tile (each covering a distinct zone). A separate set of contact electrodes is typically provided for each active material, so that the conductance of each zone of active material deposited can be measured separately, or can give rise to a separate detectable output (such as a warning sound or visual indication).

Typically, a cooling element may be provided at a position distal to or spaced from the heating means to provide a controlled temperature gradient along the sensor body.

The invention may be more clearly understood from the following description, given by way of example only, in which reference is made to the accompanying drawings, wherein:

BRIEF DESCRIPTION OF THE DRAWINGS

FIG. 1b represents a bottom view of the sensor of FIG. 1a;

FIG. 2b represents a thermal image of an upper surface of an aluminum oxide substrate known in the art and utilising the heater configuration shown in FIG. 2a;

FIG. 2c represents a thermal image of an upper surface of a beryllium oxide substrate according to the present invention and utilising the heater configuration shown in FIG. 2a;

DETAILED DESCRIPTION OF THE PREFERRED EMBODIMENTS

Figure 1A:
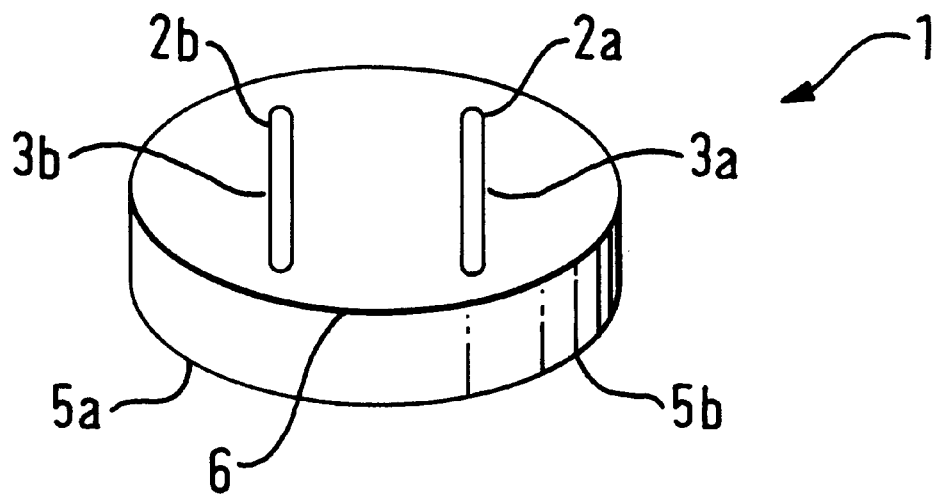
FIG. 1a represents a top view of a sensor according to a first aspect of the invention.
Figure 1B:
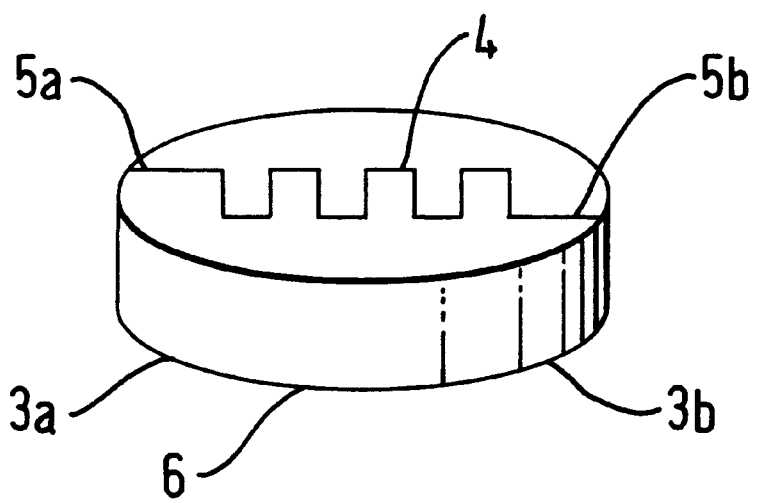

Referring to FIGS. 1a and 1b, there is shown a sensor comprising a monolithic tablet-shaped body 1 having deposited thereon a gas sensitive layer 6. On layer 6 is a pair of electrodes 2a and 2b which has respective electrode leads 3a and 3b, and heater 4 has heater leads 5a and 5b. The tablet-shaped body may, in the embodiment illustrated, be made from beryllium oxide.

Figure 2A:
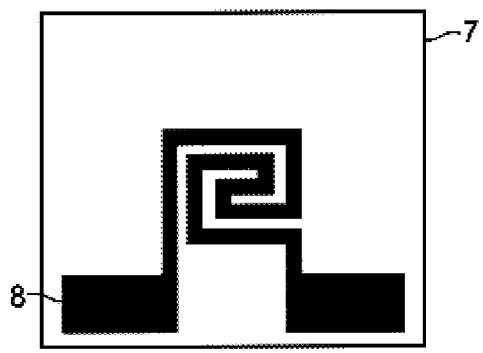
FIG. 2a represents an exemplary heater configuration suitable for use on the obverse of a sensor according to the invention.

Referring to FIG. 2a the sensor 7 is provided with a heater 8 having a configuration known in the art.

Figure 2B:
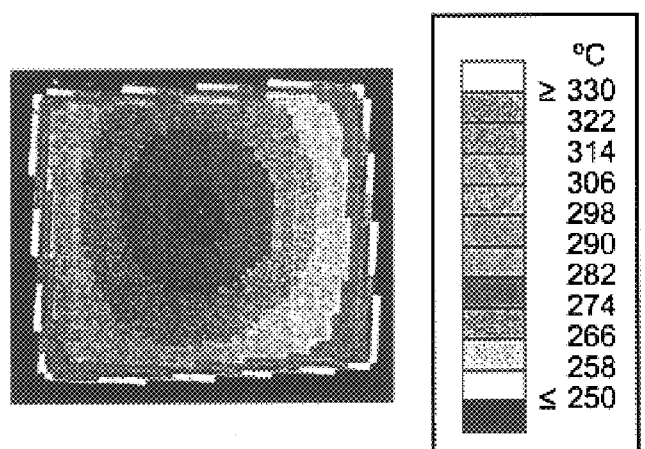
Figure 2C:
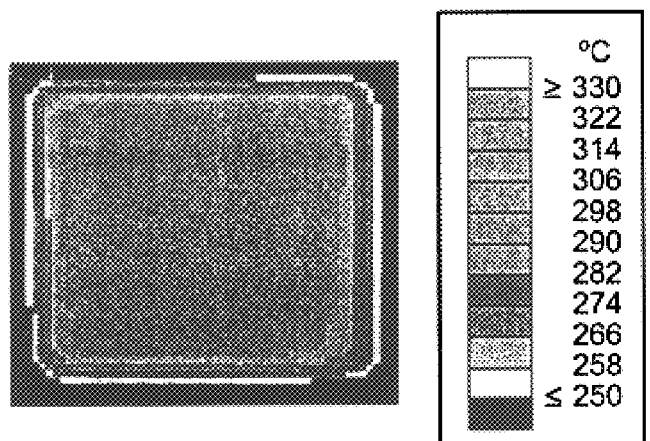

FIG. 2b is a thermal image of a sensor known in the art which utilises the heater configuration shown in FIG. 2a and a substrate of aluminum oxide. FIG. 2c is a thermal image of a sensor according to the present invention, which utilises a heater configuration shown in FIG. 2a and a substrate of beryllium oxide. The obverse surfaces of the two sensors, one having a substrate of aluminum oxide, the other having a substrate of beryllium oxide, are coated with graphite. Thermal images were then obtained using a Thermovision infra-red camera; the thermal images obtained are shown in FIGS. 2b and 2c.

It can be seen by comparison of the thermal images shown in FIGS. 2b and 2c that large temperature gradients appear in ;the aluminum oxide substrate, whereas the beryllium oxide substrate exhibits almost no temperature gradient.

Figure 3A:
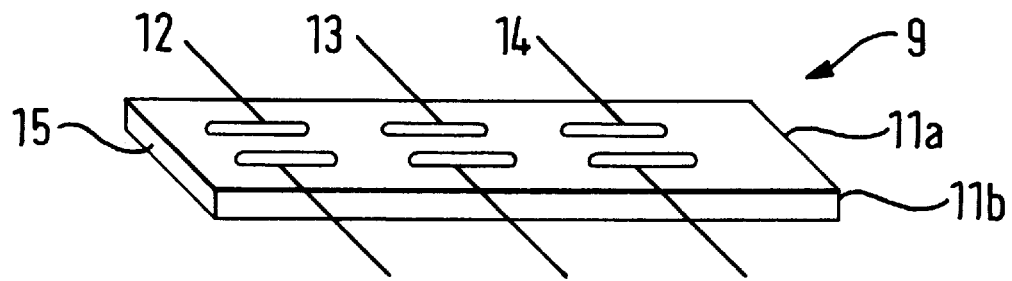
FIG. 3a represents a top view of a sensor according to a second aspect of the invention.
Figure 3B:
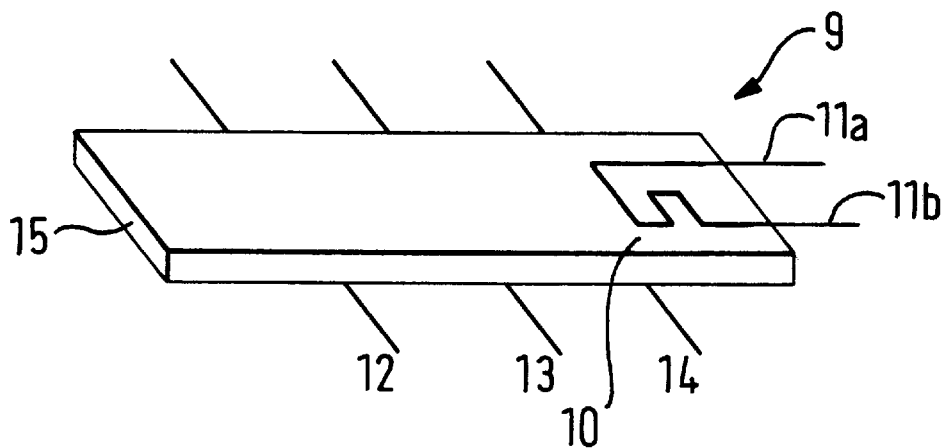
FIG. 3b represents a bottom view of a sensor according to a second aspect of the invention.

Referring to FIGS. 3a and 3b, sensor 9 which is in the shape of a monolithic tile 15 comprising beryllium oxide. The tile 15 has a coating a gas-sensitive material 16, and a heater array 10 connected to heater leads 11a and 11b, and three pairs of electrodes 12, 13, and 14. The use of beryllium oxide as a substrate and the non uniform heater array 10 creates a temperature gradient along the length of the tile. In use active materials possessing different sensitivity and/or selectivity properties (or alternatively, the same active material possessing differing selectivity properties) are deposited along multiple areas of the sensor 9; the contact electrodes 12, 13 and 14 allow the separate detection of the change in the resistance or conductance of each active material.

Figure 4:
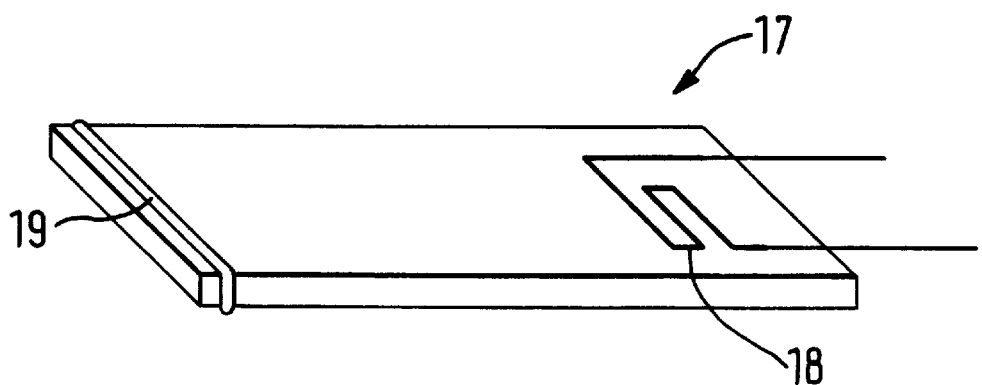
FIG. 4 represents a sensor according to a third aspect of the invention.

Referring to FIG. 4, the sensor 17 includes a heater 18 and Peltier-effect elements 19 which act as a cooling device; the addition of the cooling device further controls the desired temperature gradients obtained.

What is claimed is:

1. A gas sensor including a beryllium oxide substrate which is both an electrical insulator and a thermal conductor, said substrate being in the form of a substantially monolithic body having thereon:
   (i) an electrical resistance heating element which heats said substrate, said heating element being arranged to cooperate with said substrate to create a near-uniform temperature throughout substantially the entire sensor;
   (ii) at least one gas-sensitive active material deposited on said substrate; and
   (iii) a set of at least two spaced electrodes, each said electrode being in contact with said active material for monitoring a change in electrical conductance, resistance or impedance upon exposure of said active material to a target gas of interest.

2. A sensor according to claim 1, wherein said heating element includes an electrically conductive compound.

3. A sensor according to claim 2, wherein said electrically conductive compound includes ruthenium dioxide.

4. A sensor according to claim 2, wherein said electrically conductive compound is a noble metal.

5. A sensor according to claim 4, wherein said noble metal is platinum.

6. A sensor according to claim 1, wherein said body is substantially disc or tablet shaped.

7. A sensor according to claim 1, wherein said body is substantially in the form of an elongate tile.

8. A gas sensor according to claim 7, wherein different active materials, or the same active material having different selectivity properties, are deposited along said length of said tile.

9. A gas sensor according to claim 8, which includes separate contact electrodes for each active material.

10. A gas sensor according to claim 1, wherein a cooling element is provided at a position distal to the heating element so as to permit provision of a controlled temperature gradient across the least one of the substrate and gas-sensitive active material.

11. A gas sensor according to claim 1, which includes means for monitoring the electrical conductance between said spaced electrodes.

12. A gas sensor including a beryllium oxide substrate which is both an electrical insulator and a thermal conductor, said substrate being in the form of a substantially monolithic body having thereon:
   (i) an electrical resistance heating element for heating said substrate, said heating element being arranged to cooperate with said substrate to create a desired thermal gradient along the substrate;
   (ii) at least one gas-sensitive active material deposited on said substrate; and
   (iii) a set of at least two spaced electrodes, each said electrode being in contact with said active material for monitoring a change in electrical conductance, resistance or impedance upon exposure of said active material to a target gas of interest.

13. A gas sensor according to claim 12, wherein:
   the properties and arrangement of said heating element and the substrate ensures that the sensor establishes a near uniform temperature throughout substantially the entire sensor.

14. A gas sensor including a substrate which is both an electrical insulator and a thermal conductor, said substrate being in the form of a substantially monolithic elongate tile and having thereon:
   (i) a heating element for heating said substrate, arranged at a first end of said tile and arranged so as to permit creation of a desired thermal gradient along a length of said tile;
   (ii) at least one gas-sensitive active material for monitoring a change in electrical conductance, resistance or impedance upon exposure of said active material to a target gas of interest deposited on said tile; and
   (iii) at least two spaced apart electrodes, each said electrode being in contact with said active material.

* * * * *